(12) United States Patent
Huenerfauth et al.

(10) Patent No.: US 9,407,861 B2
(45) Date of Patent: Aug. 2, 2016

(54) USER INTERFACE TOOL KIT FOR MOBILE DEVICES

(71) Applicant: Siemens Healthcare Diagnostics Inc., Tarrytown, NY (US)

(72) Inventors: Angela Huenerfauth, Morristown, NJ (US); Benjamin Pollack, Budd Lake, NJ (US); Baris Yagci, Whippany, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/908,189

(22) PCT Filed: Jul. 31, 2014

(86) PCT No.: PCT/US2014/049027
§ 371 (c)(1),
(2) Date: Jan. 28, 2016

(87) PCT Pub. No.: WO2015/023443
PCT Pub. Date: Feb. 19, 2015

(65) Prior Publication Data
US 2016/0173816 A1 Jun. 16, 2016

Related U.S. Application Data

(60) Provisional application No. 61/866,581, filed on Aug. 16, 2013.

(51) Int. Cl.
*H04N 7/14* (2006.01)
*H04N 5/232* (2006.01)
*H04L 29/06* (2006.01)
*G06Q 10/00* (2012.01)

(52) U.S. Cl.
CPC .............. *H04N 7/14* (2013.01); *G06Q 10/20* (2013.01); *H04L 65/4015* (2013.01); *H04N 5/23206* (2013.01)

(58) Field of Classification Search
CPC ....................................................... H04N 7/14
USPC .................... 348/14.01, 14.02, 14.03, 14.04
See application file for complete search history.

(56) References Cited

U.S. PATENT DOCUMENTS

| | | |
|---|---|---|
| 5,983,369 A | 11/1999 | Bakoglu et al. |
| 6,783,367 B1 | 8/2004 | Wang et al. |
| 8,351,577 B2 * | 1/2013 | Cassanova ............. H04N 7/141 348/14.04 |
| 2002/0044104 A1 | 4/2002 | Friedrich et al. |
| 2009/0310764 A1 | 12/2009 | Gerhart |
| 2013/0066563 A1 | 3/2013 | Hengstler et al. |
| 2014/0134656 A1 | 5/2014 | Dortet et al. |

OTHER PUBLICATIONS

International Search Report for PCT/US2014/049027 dated Nov. 25, 2014.

* cited by examiner

Primary Examiner — Olisa Anwah

(57) ABSTRACT

Methods and systems facilitate troubleshooting or maintenance of in vitro diagnostic equipment. An operator of the equipment utilizes an app on mobile device to receive status information from the equipment and capture images of the equipment. Tutorials and interactive remote technical support can be provided utilizing this data.

20 Claims, 6 Drawing Sheets

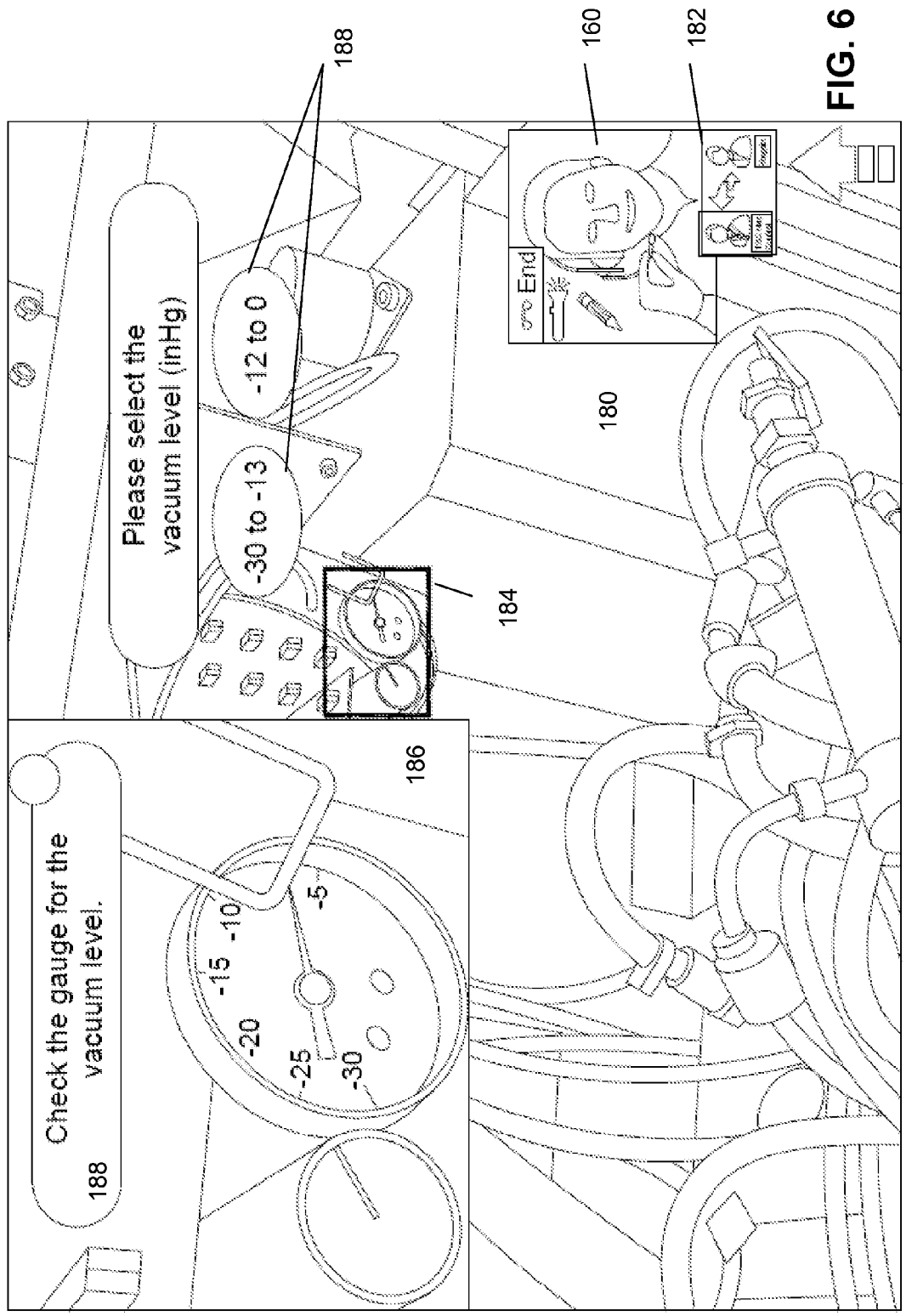

USER INTERFACE TOOL KIT FOR MOBILE DEVICES

CROSS-REFERENCE TO RELATED APPLICATIONS

This application claims priority to U.S. provisional application Ser. No. 61/866,581 filed Aug. 16, 2013, which is incorporated herein by reference in its entirety.

TECHNOLOGY FIELD

Embodiments of the present invention generally relate, but are not limited to systems for use in an in-vitro diagnostics (IVD) laboratory environment to assist local operators to troubleshoot issues with IVD equipment, including but not limited to a mobile toolkit that facilitates interaction with the IVD equipment and/or remote technical service personnel.

BACKGROUND

Laboratory equipment used in in-vitro diagnostics (IVD) often includes complicated, highly specialized, sensitive equipment that require specialized knowledge and training to operate and even more specialized knowledge and training to repair and maintain. Unscheduled, instrument downtime in the laboratory may be a cause of lost productivity for a customer/operator. Furthermore, IVD equipment is often used in hospital environments where quick sample turnaround time and high sample throughput is needed to keep hospital operations working. When an IVD instrument becomes damaged, encounters an error, or requires maintenance, the potential downtime of the instrument can be a serious problem.

Traditional service procedures for IVD equipment follow the traditional technical service escalation protocols, which can be slow in recovering from an error or getting critical equipment up and running in an efficient manner. For other technical fields, support escalation protocols may be sufficient, but the potential downtime in a lab can be unacceptable. For example, customers may first attempt to troubleshoot the issue or repair themselves. If unsuccessful, then the customer can call the Technical Support Center (TSC). Unfortunately, the aid is generally limited to verbal communication. The TSC may verbally describe a repair, while the customer must interpret the instructions over the phone. If more intensive action is needed, then a Field Service Engineer (FSE) may be dispatched to the customer site. This dispatch process may take several hours or days before a service visit is complete. During this time, the customer's instrument may be down or non-functional.

SUMMARY

Embodiments of the present invention address and overcome one or more of the above shortcomings and drawbacks by providing a mobile toolkit to facilitate maintenance, diagnostic, and troubleshooting tasks in a laboratory environment. The toolkit can utilize a combination of live help, tutorials, mobile device features, and substantially real-time sensor data from IVD equipment, such as an analyzer or laboratory automation system.

Embodiments of the present invention are directed to a system for troubleshooting IVD equipment, which includes a processor configured to receive sensor data pertaining to a status of the IVD equipment and to transmit the sensor data in substantially real-time to at least one of a mobile device and a remote technical support center. The system further includes, one or more memory devices containing software instructions to configure the mobile device to facilitate a call between a user of the IVD equipment and a representative at the remote technical support center, display one or more images to the user at substantially the same time that the representative can see the one or more images, and receive at least one command from the representative to change the one or more images displayed to the user.

According to aspects of some embodiments, at least one command comprises one or more commands to allow the representative to emphasize a portion of the one or more images. In some embodiments, the one or more images comprise at least one image captured by a camera on the mobile device. In some embodiments, the at least one command comprises one or more commands to allow the representative to instruct the mobile device to do any combination of performing a zoom function on the camera and turning on a light to illuminate the image plane of the camera.

In some embodiments, the software instructions include instructions to enable user and the representative to see one another during the call. In some embodiments, a processor at the technical support center is configured to record an interaction between the representative and the user. In some embodiments, the software instructions include instructions to present a pre-recorded tutorial to the user.

Embodiments of the present invention are further directed to a method for assisting a user in troubleshooting IVD equipment, which includes receiving sensor data pertaining to the status of the IVD equipment in substantially real-time at least one of a mobile device and a remote technical support center and facilitating, via software instructions on a mobile device, a call between a user and a representative at the remote technical support center. The method further includes displaying one or more images to the user at substantially the same time that the representative can see the one or more images and receiving at least one command from the representative to change the one or more images displayed to the user.

According to aspects of some embodiments, the at least one command includes one or more commands to allow the representative to emphasize a portion of the one or more images. In some embodiments, the one or more images include at least one image captured by a camera on the mobile device. In some embodiments, the at least one command comprises one or more commands to allow the representative to instruct the mobile device to do any combination of performing a zoom function on the camera and turning on a light to illuminate the image plane of the camera.

In some embodiments, the software instructions include instructions to enable user and the representative to see one another during the call. In some embodiments, a processor at the technical support center is configured to record an interaction between the representative and the user. In some embodiments, the software instructions include instructions to present a pre-recorded tutorial to the user.

Embodiments of the present invention are further directed to a method for assisting a user in troubleshooting IVD equipment, including receiving sensor data pertaining to the status of the IVD equipment in substantially real-time at a mobile device and requesting a first tutorial from a stored plurality of tutorials, in response to user input of the mobile device, wherein the first tutorial includes a plurality of pictures or videos to be displayed on a screen of the mobile device. The method further includes determining, based on the sensor data if a first step of the tutorial has been completed by the user and advancing to a second step in the tutorial in response to the determining step, determining, by the mobile device, if an error condition exists upon completion of a last step of the first tutorial, and connecting the user with a representative at a remote technical support center, wherein the representative receives the sensor data and can view one or more images on the mobile device screen.

According to aspects of some embodiments, the method further includes receiving, at the mobile device, one or more commands to allow the representative to draw on one or more images presented on the mobile device screen. In some embodiments, the one or more images comprise at least one image captured by a camera on the mobile device. In some embodiments, the method further includes receiving, at the mobile device, one or more commands to allow the representative to instruct the mobile device to do at least one of performing a zoom function on the camera and turning on a light to illuminate the image plane of the camera.

In some embodiments, the method further includes recording an interaction between the representative and the user. In some embodiments, the method further includes presenting to the user a second tutorial relating to a possible root cause based on the determining step.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 6 is an exemplary screenshot of a troubleshooting session using certain embodiments of the present invention.

DETAILED DESCRIPTION OF ILLUSTRATIVE EMBODIMENTS

Figure 1:
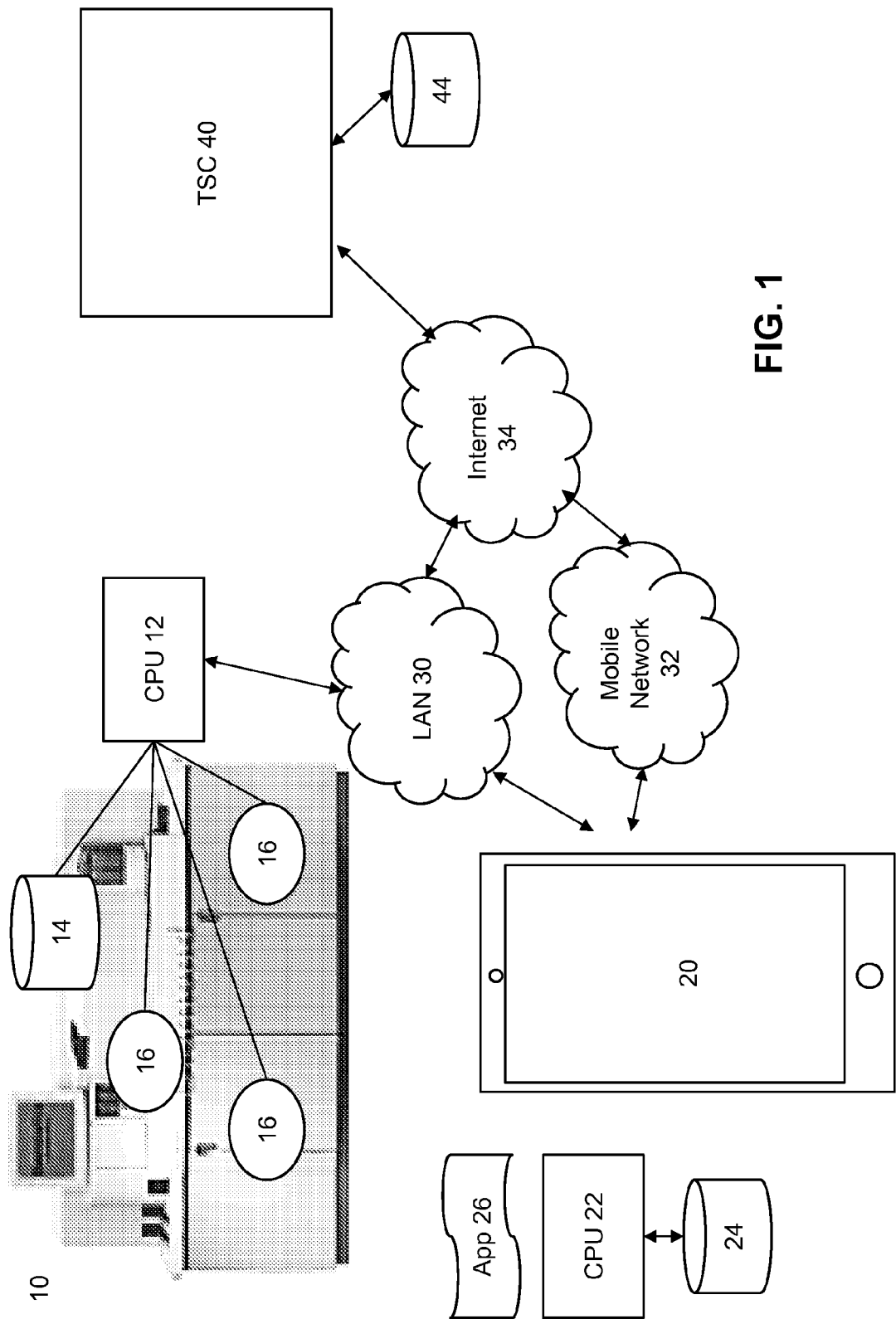
FIG. 1 is a system diagram of an exemplary system for use with certain embodiments of the present invention.

Embodiments utilize mobile technology to provide more effective communication remotely between a TSR and the customer, so that most field service calls can be replaced by an interaction with a mobile toolkit. By providing a mobile toolkit, an operator who lacks special expertise in an area related to resolving a problem can receive instruction on demand to resolve problems beyond the operator's expertise. Furthermore, the mobile toolkit can assist technical service personnel in instructing an operator with greater detail and comprehension than a traditional phone call may allow.

Technical service procedures for IVD equipment can be improved if operators/lab technicians already at the site of the IVD equipment can troubleshoot the equipment themselves or with the help of a remote Technical Support Center (TSC). If the equipment operator can solve the problem, it is unnecessary for a Field Service Engineer (FSE) to be dispatched to the customer site. This has the benefit that it can reduce the maintenance/service or warranty cost of the IVD equipment and can greatly reduce the downtime of the equipment if the operator is successful in repairing the equipment without the assistance of an FSE. If the customers/operators are offered a set of tools to aid in the troubleshooting of an instrument problem, then the customers may become more empowered and comfortable in completing the troubleshooting and instrument repair themselves. This could potentially reduce the number of phone calls to the TSC and potential field service calls for the customer. Reducing these calls potentially saves the customer and the company both time and money.

Embodiments can be used for troubleshooting, maintaining, or servicing a variety of clinical equipment in an IVD environment, such as clinical chemistry analyzers or automation systems for use with analyzers. Exemplary IVD equipment for use with these embodiments is described in further detail in PCT Patent Application PCT/US13/24331, titled "Intelligent Bidirectional Multifunctional Carrier And Integrated Automation; System For Material Distribution And Transportation," filed Feb. 1, 2013, which is incorporated herein by reference in its entirety.

Customers buying and operating IVD equipment can be provided a toolkit that is mobile to access various locations on the instrument. Mobility can be very helpful—when instruments are combined into a consolidated system or are added to a track system, the area of repair may be located at a distance from the primary display panel of the instrument. To achieve this mobility, a mobile device may be used to display the toolkit for the customer.

By providing a toolkit on a mobile device, such as a mobile phone or tablet, the toolkit can significantly reduce the level of technical expertise needed to resolve instrument service interruptions. For example, this may be accomplished by providing a mobile platform that can utilize pre-recorded tutorials, real-time instrument data, and/or live technical support to walk an operator through the process of diagnosing and addressing a problem. This can be accomplished through an application that runs on a mobile device, such as a tablet, smartphone, heads-up display glasses, etc. (which can include the operator's own personal phone or tablet). An exemplary application can implement one or more of the following features.

In some embodiments, the app and/or TSC can receive real-time status updates from the instrument, including diagnostic information/error codes, sensor states, etc. One or more processors in an IVD instrument can gather sensor data and other diagnostic information, such as state data and error codes, from the instruments, (and in some embodiments, from sensors and processors in other related IVD equipment that work with the instrument, such as automation tracks or analyzers). This information can then be provided in substantially real time as it is gathered, at a polling/transmission interval, as a data stream, or on demand, across a local network or the internet using secure/suitable transmission protocols, such as HTTPS, SSL, etc., to the operator's phone and/or to computers at the TSC. This can allow real-time feedback to the technical support representative (TSR) and/or the operator trying to troubleshoot the instrument. Status information received can be used by the application on the operator's mobile device to relay information in substantially real time to the operator, be sent from the application across the internet to the TSR, and/or may be analyzed by the application to affect the script of a tutorial, determine what steps should be undertaken, determine if the problem has been resolved, identify the problem, suggest tutorials or next steps, determine if a step has been completed, etc.

In some embodiments, an intelligent log parser can identify multiple symptoms in the status information log to identify a single root cause. For example, experiential logic can identify correlations in the status that can relate to a single root cause and assist the operator in identifying and correcting a root cause. For example, an aspiration failure, a positional failure, and a motor failure error for a pipette arm can relate to the failure of the motion system for that pipette arm, allowing the application to suggest looking for blockages in the motion system and then assisting the operator in identifying any problems with the motor and related motion systems for the pipette arm. Furthermore, in some embodiments, the real-time nature of the status log can assist in identifying which errors happened first. This determination can be made by the app on the operator's mobile device and/or processors at the TSC, and can be automatic to aid in the diagnosis by the TSR or operator.

In some embodiments, an app on a mobile device has access to a database of pre-recorded tutorials, using either annotated static images or videos that demonstrate how to diagnose or resolve a problem. For example, users can access a series of photos or pictures from the static image library and dynamic videos from the online help to aid in the troubleshooting and repair process. The static images may be stepped through with a NEXT STEP or GO BACK button, while the dynamic videos may be displayed by pressing the SHOW DEMO button. Tutorials can include any combination of image, text, and video information to assist an operator in resolving a problem. These tutorials can include a step-by-step approach to debugging the problem and can be presented in a wizard format.

In some embodiments, tutorials and/or written documentation can respond to the real-time status updates from the instrument. For example, if a sensor detects a jam, then the toolkit can automatically open or suggest a tutorial on clearing the jam. At each step, the toolkit can confirm, based on changes to the status information of the equipment, that the step has been successfully completed and then automatically advance to the next step in the tutorial. If the sensor confirms that the operator has successfully followed the instructions and cleared the jam, but a problem still exists, then the toolkit would close the "Clear Jam" tutorial and open a new tutorial that represents the next most likely root cause.

In some embodiments, the toolkit can provide the ability for the operator to request live support from a technical service representative at any time by pressing the "CALL TSC" button in the app. Activating the "CALL TSC" feature enables an additional set of tools including one or more of the following. The operator and service person can talk to each other through either a microphone and speaker(s) embedded in the mobile device or a headphone worn by the operator which is connected to the mobile device. In addition, in some embodiments, the following features can be provided.

In some embodiments, the operator and service person can see each other using two-way webcams. Operators may find it helpful to have the service person that you can speak to directly and you know just have that face-to-face interaction.

In some embodiments, the remote service person can view what the operator is seeing through a camera on the mobile device.

Two-way command functions (control can be transferred between the remote service person and operator) can be provided, including the following.

Two-way draw: Depending on who has control of the screen (remote service person or operator), that user can draw on his screen and be seen on the other user's screen. An exemplary use case includes where the camera and capture the issue on the instrument and then the operator can circle something that may be an area of interest or that he understands the operator is referring to. The TSR could then take control of manipulating the image to verify, or to circle an area where the TSR wishes the operator to look at. Sharing images and allowing either party to manipulate the image can provide a visual way of helping somebody with a problem versus just describing the steps.

Two-way flashlight: Depending on who has control of the screen (remote service person or operator), that user can control the flashlight on the customer's mobile device. This feature may be useful when discussing areas within the equipment that may be in shadows or otherwise difficult to see. The operator or TSR can turn on the flashlight or related illumination to make it easier to view internal portions of equipment. Many modern mobile devices have a flash feature adjacent to the mobile device's camera that can be used as a flashlight or to illuminate an image to capture images in low light applications.

Two-way zoom: Depending on who has control of the screen (field service or operator), that user can control the zoom level of the camera which shows what the operator is seeing. For example an operator can use his mobile device to pinch to zoom into a part of the image that he wishes to discuss with the TSR. Similarly, the TSR can remotely zoom the image to draw the operator's attention to a portion of the image for further discussion or emphasis.

The live interactions between operators and TSC representatives can be recorded and stored in a TSC knowledge database along with metadata about the service incident, ex. what was the issue, was it resolved successfully, etc. Data mining can be used on the metadata to identify wide spread problems in the field and identify areas in need of engineering improvements or enhanced tutorial development. The recorded interactions can be used by engineers at the manufacture of the equipment as part of root cause analysis and by customer support as the basis for new curated tutorials.

By providing any subset of these features, a toolkit that utilizes an app on a mobile device of an operator can provide substantial benefits over traditional manuals and over-the-phone technical support. Benefits may include reduction of TSC phone calls and FSE visits to the customer sites and increase the effectiveness of the field service efficiency for topics they are not well versed. FSEs can also use the toolkit themselves for training or when visiting customer sites to get additional help from the TCS to expedite the solution of problems.

Embodiments may address a common problem with traditional telephonic TSR sessions. During typical telephonic sessions, there is generally no way to get information from the customer site to the TSR, other than by the descriptions conveyed by the operator at the customer site. Embodiments may supplement this verbal information with image or video information from the operator's mobile device, as well as status information gathered by a processor within the equipment being serviced. The combination of voice, video/image, and real-time status information can effectively extend the telepresence of the TSR to the customer site in close approximation to the effectiveness of having a FSE at the customer site. By putting this information into the hands of the TSR and providing a way to convey information to the operator, the operator can resolve problems with greater expertise than he might be trained for. Furthermore, where an operator's lack of training in repairing the instrument limits his vocabulary or ability to describe problems or to comprehend instructions from a TSR, the two-way communication features of the mobile toolkit can increase this comprehension of both the TSR and the operator at the customer site.

Some embodiments may be more cost effective and easier to implement than a full Augmented Reality (AR) technical support kit. The cost of implementing such a full solution can be very high. However, some embodiments may utilize AR tutorials to assist operators in resolving common problems. Some embodiments may act as a stepping stone to a full AR solution by providing recordable TSC support events that include user feedback, equipment status information, and mobile device camera feeds. These events can help the technical support team at an equipment manufacturer understand the potential benefits of certain AR tutorials, identifying the most common errors that operators encounter, the relative ease by which operators can solve these problems with guidance, and learn the correlation of sensor/status information to the problems and steps undertaken by the operators in resolving equipment problems.

If the manufacturer or toolkit provider pursues a full AR solution, recorded interactions can serve as the basis for the AR content. Metadata associated with recorded interactions can be used to prioritize the development of AR content for frequently occurring problems that can be effectively resolved through simple walkthroughs. This approach can minimize the cost of AR content creation and provide the highest return on investment. Prior art AR solutions have typically been designed from scratch using a script developed as a best-guess by service personnel, often without the benefit of recorded interactions with operators. Accordingly, prior art AR approaches can be expensive to develop and may be of limited utility. By mining the information provided by recorded interactions through the mobile toolkit service personnel can develop more meaningful AR tutorials or other static or dynamic tutorials based on observations of past interactions and common comprehension issues faced by operators in the field.

In addition, by providing a mobile toolkit that utilizes an operator's mobile device, which can include a camera and screen, AR tutorials can utilize the combination of camera and screen to augment the images displayed to the operator without requiring custom or expensive virtual reality headsets to be employed. For example, by utilizing conventional image processing and recognition techniques, images captured by the operator's camera can be analyzed to identify salient features related to portions of the equipment that relate to the AR tutorial content. Information can then be displayed on the mobile device's screen to augment the image and provide information to the operator in the context of the image.

Some embodiments of the mobile toolkit may include the ability to display the real-time status information to both the TSR and the operator, to further assist the operator and resolve the problem. Curated AR tutorials may also be available to the operator to assist the operator where he chooses not to call the TSR or a TSR is unavailable. Intelligence within an AR tutorial may allow the story all to interact with captured images and respond to changes in status information in the equipment in a manner similar to that of a qualified TSR, allowing the tutorial to provide a first line of defense for common problems before a TSR is involved. In some embodiments, a tutorial may use stored static images to instruct the operator, while in other embodiments, an AR tutorial may respond to video or images captured by the operator's mobile device camera and highlight portions of the image to convey instructions to the operator. Methods for highlighting portions of the image may include use of color, zoom, highlighting, drawing shapes or boxes on the image, arrows, text, etc. These methods may also be used by the TSR and the operator when discussing images.

In some embodiments, the mobile toolkit can provide access to the repository of documentation, in addition to tutorials.

At the TSC, audio, video, commands, and status information can be recorded for each technical service interaction. These interactions can be tagged with metadata automatically, or by instruction of the TSR, so the interactions can be cataloged based on the type of problem, symptom, resolution, etc. By tagging these interactions, the metadata can be mined, providing a repository of past interactions for each type of problem, allowing a human or artificial intelligence to identify what techniques works to resolve the problem, as well as any problems that were encountered with the instrument or with the comprehension of the operator. These tags may also allow a user community to search for recorded service calls to use as tutorials when these users have a similar problem, allowing users to resolve problems when TSRs are unavailable.

Similarly, setbacks during the troubleshooting process can be identified, such that common setbacks can be identified and addressed in any tutorials that may be developed to solve common problems. Statistical analysis of the problems or resolutions can be accomplished by mining this metadata, which may be useful in identifying the most common problems and the typical TSR resource cost for resolving each type of problem. This may be helpful in identifying which problems could be solved in a cost-effective manner if static or dynamic tutorials are developed, or if an AR troubleshooting application would be worth the associated cost to the manufacturer of the equipment. By providing metadata and recorded interactions that can be mined in this manner, the mobile toolkit can evolve over time, allowing an equipment manufacturer to start with a basic toolkit and develop curated tutorials and artificial intelligence AR troubleshooting applications for the most common problems, as well as provide access to the user community to recorded sessions by other users to guide these users through the problem when a TSR or curated tutorial is unavailable.

There are multiple ways in which recorded in tag technical interactions can be mined to assist in developing tutorials or other curated content. First, interactions may be statistically mined to identify common problems and common solutions, including the resource cost to the TSC to resolve the problem. Second, interactions may be mined manually or via artificial intelligence learning techniques to correlate common symptoms with common problems. This can be helpful in developing root cause analysis, as well as developing dynamic scripts for tutorials or TSRs to resolve problems and meaningfully interpret status information from the instrument being serviced. Furthermore, an operator or TSR may have access to a repository of past recorded interactions, allowing the viewer to search by symptoms to view how those symptoms have been addressed in the past. This can be a helpful training procedure for operators or TSRs. Finally, when an equipment manufacturer has decided to develop a tutorial or AI AR troubleshooting application, past interactions between operators and TSRs can be viewed by the developers of these tutorials and AR applications to more fully understand the issues will be addressed by the tutorial work troubleshooting application.

Developing artificial intelligence applications to solve specific technical issues can be an expensive process, requiring many man-hours dedicated to identifying parts of a decision tree and the underlying logic to be used in aiding the operator in troubleshooting a problem. Accordingly, many technical problems may not be important enough to warrant the cost of developing artificial intelligence related to solving these technical problems. By mining an data relating to past experiences in troubleshooting problems, the most relevant problems, such as those that occur most often or those that would otherwise be expensive for a TSC to repeatedly solve using human TSRs, can be identified. This can allow a business to determine whether there is a business case for creating specific AI or AR content related to that problem.

By providing a troubleshooting toolkit that can operate with a mobile device, an operator can troubleshoot using a screen that he can move around the laboratory environment, as well as a camera that can be conveniently used during the troubleshooting operation. This allows an operator to quickly and intuitively indicate to a TSR what he is looking at, greatly increasing the efficiency of troubleshooting conversations. Similarly, now that mobile devices generally have front facing cameras, TSRs and operators at customer sites can have face-to-face video chats as part of the troubleshooting session. Furthermore, because mobile phones and tablets are ubiquitous, operators can generally utilize the toolkit without purchasing additional equipment, using their own mobile devices, which will be readily available to the operator. Accordingly, in some embodiments, a mobile toolkit is available for use with multiple mobile operating systems, allowing the operator to choose which mobile devices to use with the toolkit. The toolkit can include an application that downloads and installs on the operator's mobile device. Accordingly, equipment manufacturers can focus on developing a simplified software application that allows the functionality necessary for troubleshooting, without developing additional hardware. Furthermore, the toolkit can be upgraded via convenient software downloads as new features become available.

Many prior art AR tools require expensive headsets, which are custom-made for the AR application. By utilizing mobile devices with cameras and screens, AR functionality can be developed over time without requiring the purchase of additional expensive hardware or requiring a manufacturer to develop this hardware, which may be outside the manufacturer's expertise. Furthermore, by providing an application that operates on standard mobile operating systems, third parties can develop the mobile toolkit for these manufacturers, allowing technical service to be easily added to new equipment without requiring manufacturers to develop additional expertise. It should be appreciated that future mobile devices can include mobile devices having headsets, such as Google Glass, as these devices become more ubiquitous.

It should be appreciated that the images that are presented to a TSR and to the operator on his mobile device can be images that are captured with the mobile device camera or images that are pushed from the TSC to the operator, such as images in a catalog of file images of the equipment being diagnosed. The operator, with the downloaded images in hand, can easily view the image and identify the physical location of the matching components of the instrument being diagnosed, without requiring extensive and confusing descriptions of the parts of interest from the TSR. This can streamline the interaction. Similarly, the operator may access stock images from a database to discuss a problem with the TSR, or the operator may capture video or still images via the camera of the mobile device to quickly provide the image for discussion.

Furthermore, in some embodiments, the TSR may push images or tutorial content to the operator for display on his mobile device. For example, during a discussion, the TSR may identify a stock tutorial that may be helpful. The TSR can push this tutorial to the operator's mobile device to allow the operator to work through the troubleshooting process. Similarly, the TSR can pull up relevant images for display that may aid in making the points that the TSR is making during the troubleshooting process, to aid in the comprehension by the operator. Similarly, the TSR may push URLs to the operator, allowing the operator to open links via a web browser or other online tool, so that the operator can find additional information that may be helpful. Furthermore, in some embodiments, a database of tutorials can be provided that is accessible to both the TSR and the operator, allowing either the operator or the TSR to request the display of tutorial content on the mobile device of the operator.

In some embodiments, in addition to utilizing the features of the mobile device that allow the exchange of information between a TSR and an operator to be improved over a traditional phone call, sensor and status information from the equipment being diagnosed or repaired can also be exchanged between the customer site and the TSC. In some embodiments, this sensor and status information is gathered via one or more processors within the equipment, providing a substantially real-time log of status information, which can be packaged and sent via a network to the TSC and/or to the mobile device. Information can be updated in real time during the technical service call, allowing the TSR and operator to have real-time feedback from the equipment about the effectiveness of the steps being undertaken. This can greatly increase the efficiency of technical service calls.

Status information can be gathered from any relevant source within an instrument being troubleshot. This can include any type of sensor, such as temperature, humidity, pressure, voltage/electrical, open/closed switches, processor state, memory state, network state, error state, etc. Processors collecting this information can gather any reasonable information about the status of the analyzer, such as the operating conditions, whether there is an error, physical state (e.g. door ajar, components installed, configuration information, electrical state, etc.) Status information, from sensors or from memory that records status and configuration information about an analyzer can be read and manipulated by a processor in the analyzer. This processor can make this information available to a network interface (e.g. by transmitting the information across the Internet automatically or upon local or remote request), allowing remote technical support personnel to request or receive information about the current state of the analyzer. This information can be presented in substantially real time, allowing remote support to have sufficient state of information to assist in diagnosing a problem and confirming that a user of the analyzer has completed a task as the representative walks the user through the trouble shooting process. Similarly, this information can be presented to the operator's mobile device via a LAN/local Wi-Fi network, or through the internet, allowing the operator or logic in a tutorial to access the status information during the troubleshooting process.

Collecting status information from the instrument being troubleshot can allow this information to be further analyzed by software at the TSC or on the operator's mobile device. For example, software can correlate sensor signals to the root cause of a problem. Often when something has an error, there are ten different other errors detected. By linking in these sensors through this whole diagnostic process and categorizing the solution and monitoring changes as each step goes along as the operator follows the diagnostic process, changes in the sensors can reveal the actual root cause.

By recording diagnostic sessions over time from multiple customer sites, software at the TSC can learn over time to build up an analytical expertise via AI methods to identify a correlation between the sensor output in a given state and the likely failure. And over time, software mining data at the TSC will develop better predictions. Furthermore, by recording the sensor data, error information, etc. to create a log for a given customer IVD instrument, errors can be tracked to determine if a maintenance procedure effectively solved a problem. By correlating the steps that that have been taken to correct an error, the final root cause can be better tracked for each customer instrument, and the knowledge base for resolving future problems can be increased. From this, generating tutorials by recording customer interactions can be facilitated in some embodiments.

FIG. 1 shows an exemplary system for use with embodiments of the troubleshooting mobile toolkit. In this system, an exemplary IVD instrument includes an analyzer, which is designed to handle IVD testing of a plurality of patient samples at high throughput. The analyzer includes one or more CPUs 12 which are capable of communicating with the network via a network interface. CPU 12 can gather status information from memory 14 and sensors 16 within the analyzer. Sensors 16 can monitor any relevant conditions in analyzer 10, as per the designer's choice when designing the analyzer. The sensors can include any sensors discussed throughout, including switches that indicate a physical state, positional sensors, temperature sensors, open-door sensors, etc. Memory 14 can include a status log of computational states, sample states, operating conditions, a log of sensor data, etc.

Mobile device 20 is an exemplary mobile phone or tablet In the possession of the operator of analyzer 10. Mobile device 20 includes a CPU 22 and memory 24. A mobile device toolkit application 26 can be installed on mobile device 20, stored in memory 24 and executed on CPU 22. Application 26 may be downloaded onto device 20, allowing the mobile devices to be updated to include the mobile toolkit. Mobile device 20 can include a screen and one or more cameras, such as a rear facing and front facing camera. A combination of a rear facing camera and screen can allow an image of the environment behind the mobile device to be displayed on the screen and shared via the network interface of the mobile device. This image can be enhanced by turning on lights on the back of the mobile device, zooming the image captured by the rear facing camera, or by overlaying shapes or other information onto the image on the screen of mobile device 20, such as by drawing. A combination of a front facing camera and screen can facilitate a two-way video chat with a TSR.

Memory 24 can include a plurality of images captured via the one or more cameras of mobile device 20. Memory 24 can also include a repository of tutorials that are accessible to the operator when troubleshooting issues with analyzer 10. Memory 24 can also store status information received from analyzer 10.

Analyzer 10 and mobile device 20 can communicate with one another and with TSC 40 via a plurality of networks. LAN 30 can include a Wi-Fi network in the local laboratory environment, allowing analyzer 10 and mobile device 20 to communicate locally. Where a mobile device has Wi-Fi disabled, analyzer 10 may communicate via LAN 30, Internet 34 and the mobile network 32 to which mobile device 20 is subscribed. (It should be appreciated that a mobile device need not be capable of operating on a mobile network.) The communication between analyzer 10 and mobile device 20 can be useful for conveying status information gathered from the analyzer via CPU 12 to mobile device 20, allowing the operator to have real-time status information at his fingertips while he walks through the troubleshooting process.

Similarly, analyzer 10 can communicate to convey status information gathered via CPU 12 via LAN 30 and Internet 34 to TSC 40. This allows TSC 40 to be remote from a laboratory setting. TSC 40 can also communicate with mobile device 20 via the Internet 34 and at least one of LAN 30 and mobile network 32.

TSC 40 and mobile device 20 can communicate audio, such as via voice over IP or a voice network, share images across an IP network, share status information from CPU 12 across the data network, facilitate and video chat between an operator of mobile device 20 and a TSR that TSC 40, exchange data, such as tutorial information or URLs, or exchange commands to manipulate images in a collaborative fashion to facilitate effective communication of the troubleshooting process.

TSC 40 can be a data center, having servers and workstations for a plurality of TSRs. TSC 40 can be a cloud-based data center, and need not be limited to a single facility. TSC 40 has access to database 44, which can be used for recording and storing troubleshooting sessions. Database 44 can also include a repository of manuals and tutorials which the TSR can rapidly access and send this information to mobile device 20, allowing the operator of mobile device 20 to easily receive technical instruction and tutorial information during the troubleshooting session with the TSR.

Figure 2:
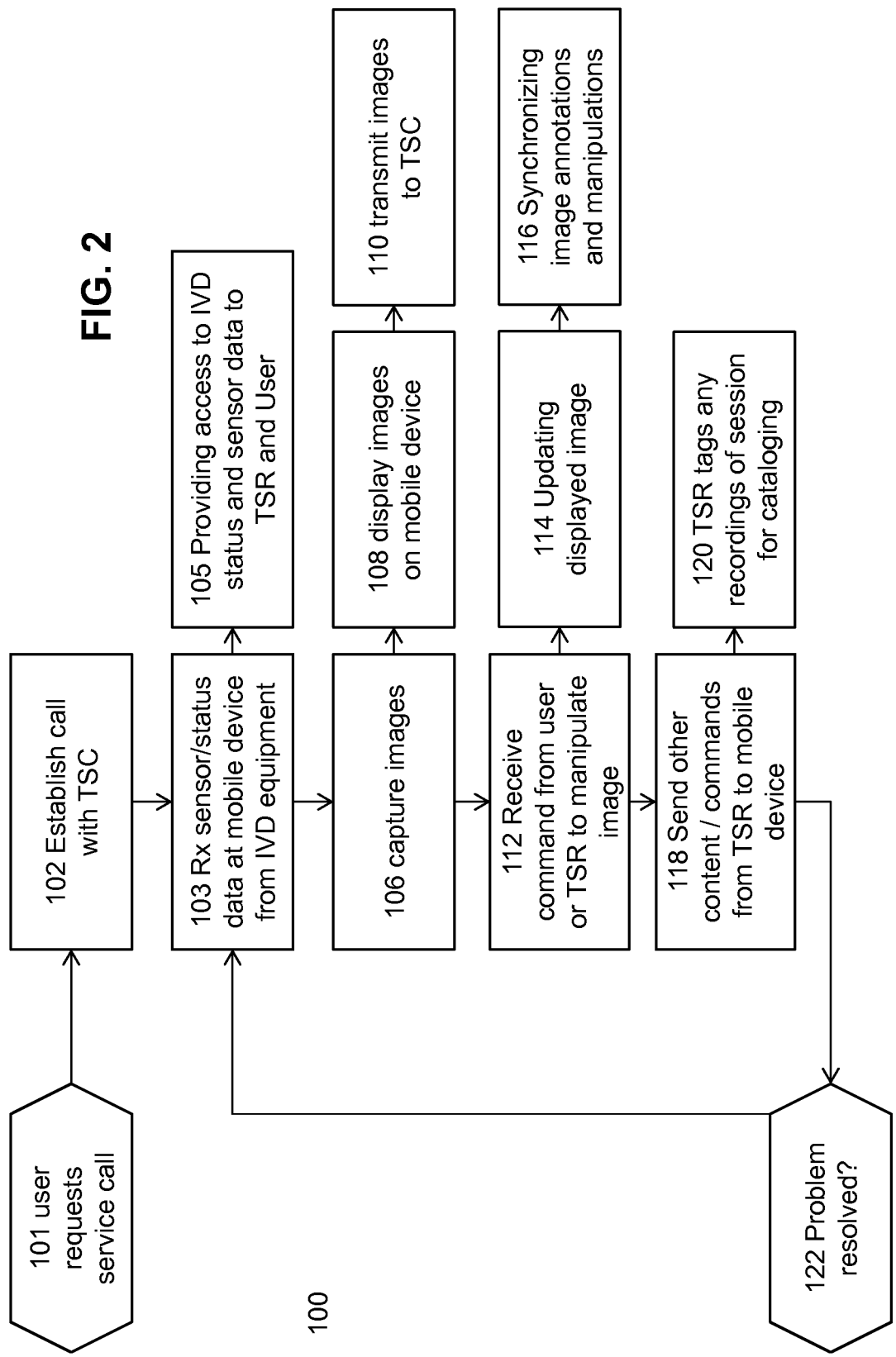
FIG. 2 is a flow chart of an exemplary method for use with certain embodiments of the present invention.

FIG. 2 shows an exemplary process 100 for handling service calls between an operator of mobile device 20 and the TSR at TSC 40. At step 101, the operator requests a service call via the application on mobile device 20. This step can be initiated by selecting an icon or menu item within application 26. At step 102, mobile device 20 will establish a call between TSC 40 and mobile device 20. This call can be via data and/or voice networks. The call can be established using secure protocols, such as SSL or HTTPS. At TSC 40, a TSR is selected to handle a call and connected with the operator of mobile device 20.

At step 103 mobile device 20 receives status information from the analyzer 10. Similarly, at step 105 TSC 40 receives access to the status information from analyzer 10. In some embodiments, analyzer 10 communicates with only one of mobile device 20 and TSC 40, and the recipient information can share it with the other. Similarly, upon receiving status information, mobile device 20 or TSC 40 can selectively display this information to the operator and TSR. Applications on these computing devices can also access this sensor and status information to apply logic to the status information to establish a root cause or to verify the effect of steps taken during the diagnostic process.

Once the operator and TSR have access to status information from the analyzer and have established a call, the operator can capture images at step 106 using his mobile device to visually indicate to the TSR what he is observing. At step 108, images captured via one or more cameras on the mobile device can be displayed to the operator on the screen of mobile device 20. At step 110, mobile device 20 transmits these images to TSC 40 via conventional network means. This allows the TSR to also see on a computer display the image being shared by the operator.

At step 112, the TSR or operator can manipulate the image. Step 112 can be a collaborative process, allowing either party to control manipulation of the image, such as zooming on certain portions, highlighting certain portions, drawing on the image, turning on the flashlight to illuminate certain parts of the image field, etc. At step 114, the mobile device receives a command either via the touchscreen interface from the operator, or via the network from the TSR and updates the image displayed on the screen of the mobile device. At step 116, changes, manipulations, and annotations to the image are synchronized across the network so that the screens of the mobile device and the terminal being operated by the TSR both display similar image information, allowing the two parties to discuss the same image.

At step 118 the TSR can send other content or commands to the mobile device via the network. This can include pushing tutorials, bringing up stock images or manual information, displaying specific instructions on the screen of the mobile device in tutorial fashion, etc. Similarly, the TSR can manipulate the images on the mobile device screen, allowing the TSR to emphasize certain portions of the image to aid in communication.

During the troubleshooting session or shortly thereafter, at step 120, the TSR can save a recording of the troubleshooting session and associate tags with that troubleshooting session that may be useful in cataloging the recording. For example, if a service call relates to solving a vacuum error within analyzer 10, the TSR may tag a recording of that service call with the model number of analyzer 10, the serial number or customer site, identification of the purpose of the service call, any error codes sent from analyzer 10, an indication of whether the errors were resolved, etc.

At step 122, the operator or TSR can manually establish whether or not the problem was resolved, or status information obtained from analyzer 10 can indicate automatically whether the problem was resolved. If so, the service call can end; if not, the troubleshooting process can continue at step 103, continuing to stream status information from analyzer 10 to TSC 40 and mobile device 20, while the operator of the analyzer and the TSR can continue discussing the problem and sharing and manipulating images to aid in that discussion.

Figure 3:
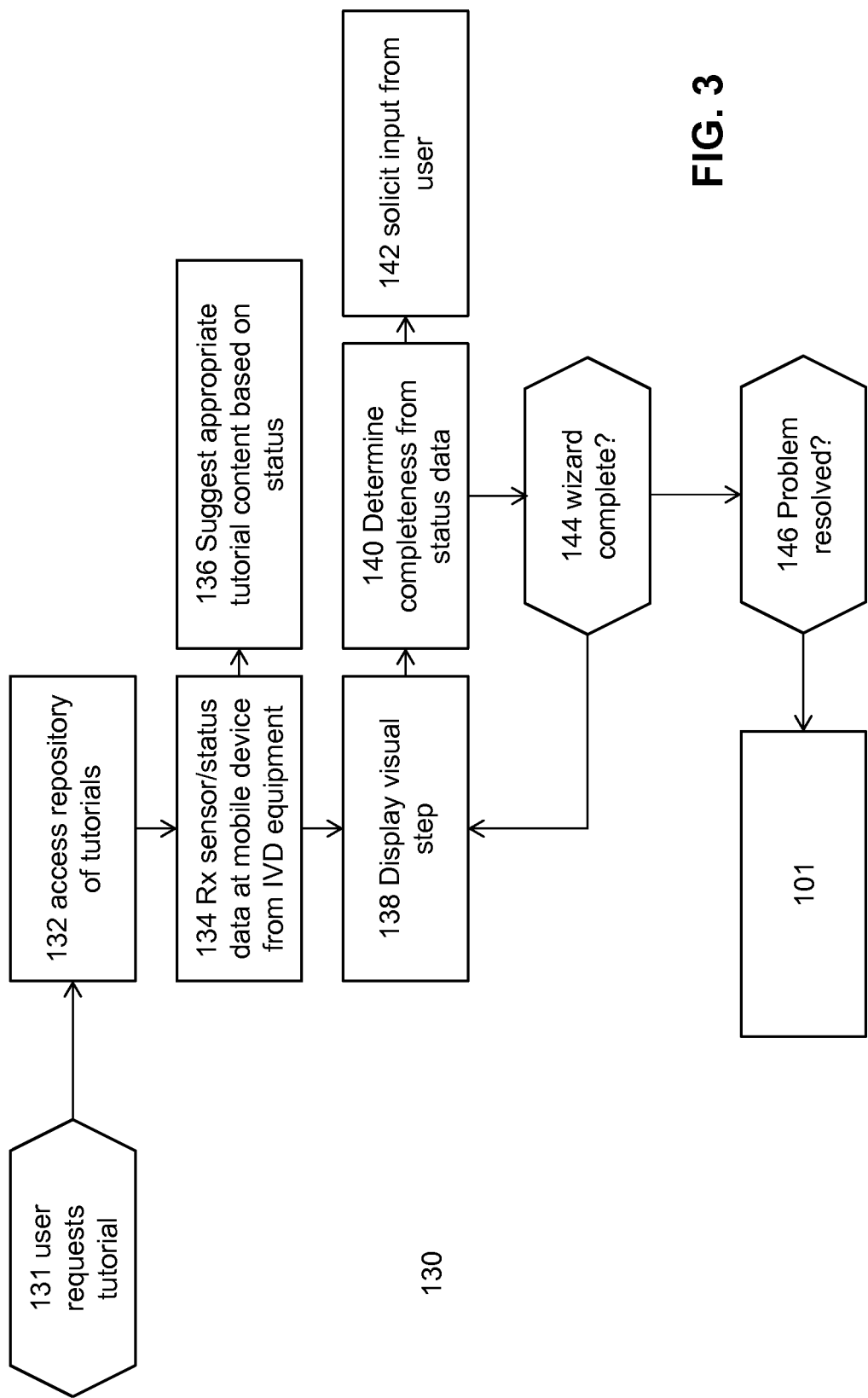
FIG. 3 is a flow chart of an exemplary method for use with certain embodiments of the present invention.

FIG. 3 shows an exemplary process 130 for executing a tutorial on mobile device 20 to walk through a diagnostic procedure in an automated fashion. At step 131, the operator of analyzer 10 requests tutorial content. This can be done via a button on the screen of mobile device 20 as part of application 26. At step 132, application 26 provides access to a repository of tutorials. This repository can be local, such as tutorials stored in local memory 24, or can be accessed via a network in a remote repository, such as database 44 at TSC 40.

At step 134, application 26 receives sensor and status data from the IVD equipment, such as status information from processor 12. At step 136, in some embodiments, application 26 can suggest the appropriate tutorial content in response to this status information. For example, where status information indicates a type of error, application 26 can automatically recommend tutorials related to that ever.

Upon automatically or manually selecting tutorial content, at step 138, the first step of the tutorial is displayed. This step can provide instructions to the operator that identify the specific tasks he must undertake to troubleshoot the equipment. This step can be displayed visually with words or a brief video on the display of the mobile device. At step 140, in response to real-time updates of sensor in status data received from the IVD equipment, the tutorial can determine whether the tasks have been carried out. For example, where a step requires opening a door on the IVD equipment, a door sensor can indicate to the mobile device that the operator has properly opened the door. A visual indication of the success of this step can be displayed, or a next step can be advanced automatically.

In some instances, sensors may be insufficient to indicate the completeness of a step. Accordingly, at step 142, the operator may optionally respond to an inquiry from the tutorial to indicate that the step has been performed. At step 144, after each step has been performed, application 26 determines whether or not additional steps in the tutorial are needed. If so, the next step is displayed at step 138. If not, at step 146 application 26 determines whether or not the problem has been fully resolved. If so, the tutorial can exit. If not, application 26 can suggest returning to step 101 to request a service call be initiated. Furthermore, if a root cause can be determined from the fact that the tutorial was unsuccessful, the method can return to step 136, and suggest another tutorial related to a suspected root cause. Once all tutorials related to possible root causes have been considered, the app can return to step 101 and suggest calling the TSC.

Figure 4:
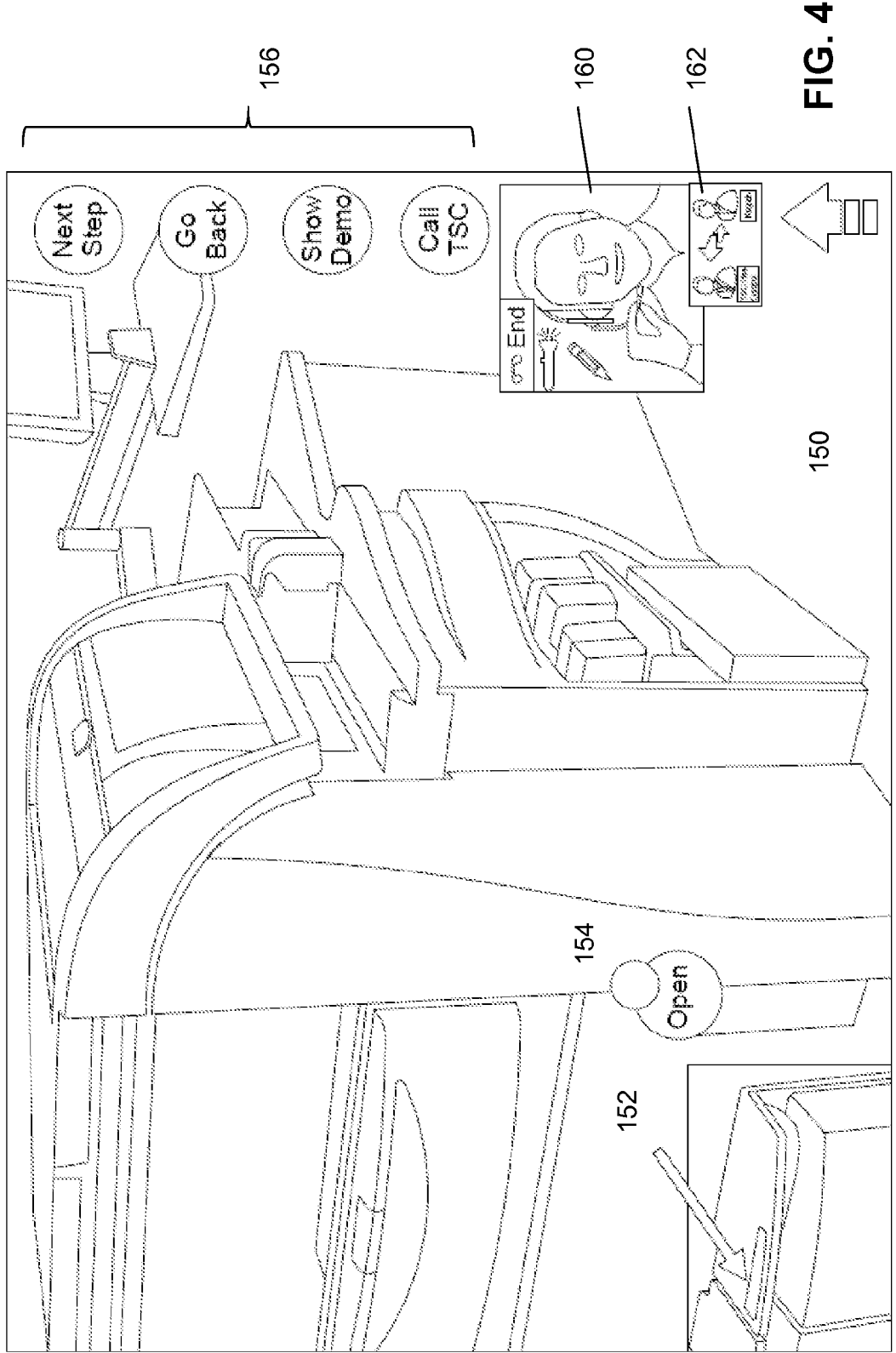
FIG. 4 is an exemplary screenshot of a troubleshooting session using certain embodiments of the present invention.

FIG. 4 shows an exemplary screenshot from a mobile device, during a technical support troubleshooting session. Image 150 can be an image captured via the mobile devices camera or can be an image selected by a TSR to illustrate steps to be performed. Arrow 152 can be drawn on the image to indicate a drawer to be opened. Instruction bubble 154 can be overlaid on the image to instruct the user of the steps to be performed. In this case, the TSR wishes to instruct the user to open the drawer indicated by arrow 152. In some embodiments, instruction 154 can be manually selected by the TSR, while in other embodiments, instruction 154 may be part of a predetermined tutorial or script that is being walked through by the user and TSR. Buttons 156 include a plurality of options for the user to select that can help navigate through the troubleshooting process. For example, using the "next step" or "go back" buttons, the user can advance or rewind tutorial steps or the steps selected by TSR. "Show demo" can be used to pull up additional content, such as a video, where a user does not understand the step. The "call TSC" button can be used to initiate a call with the TSC. Accordingly, the screenshot shown in FIG. 4 may be similar during a live call with a TSR or during a tutorial.

Box 160 can include a video image of a TSR handling the troubleshooting process. This can allow a user of application 26 to have a face-to-face videoconference with the TSR to enhance the experience. Control and indicator buttons in box 160 can also be used to aid in discussion with TSR. For example, a button may be used to end the call. A flashlight icon may be selected to turn on illumination on a mobile device and may indicate that the flashlight has been turned on by the TSR or user. A pencil icon can be used to initiate drawing on the image to communicate ideas to the TSR, and the pencil icon may be illuminated when either the TSR or user is currently drawing on the image. Status box 162 may indicate which party, the user or the TSR, has control of drawing and image manipulation features any given moment. It should be appreciated that the interaction shown in FIG. 4 could occur during a tutorial or during a live troubleshooting session.

Figure 5:
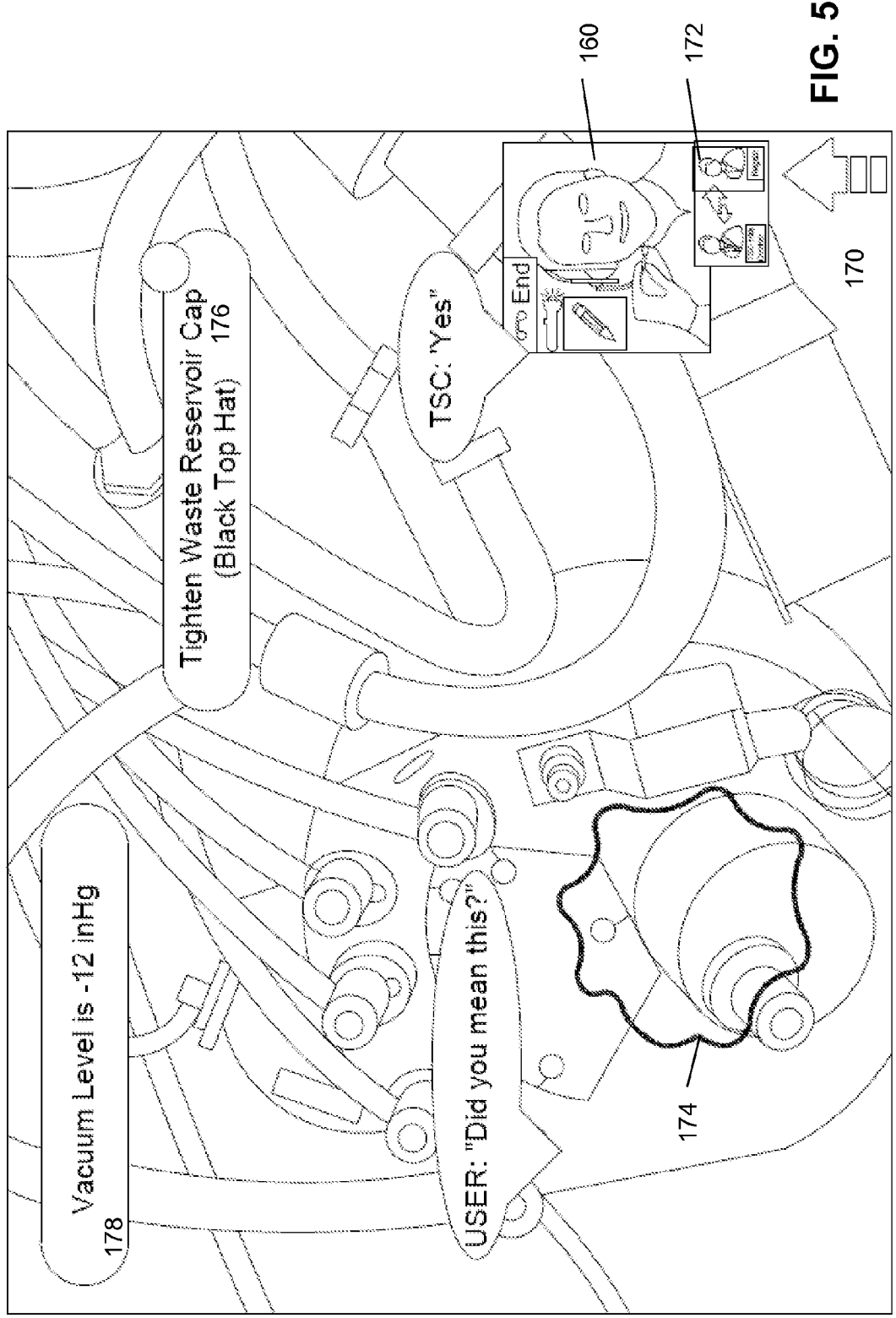
FIG. 5 is an exemplary screenshot of a troubleshooting session using certain embodiments of the present invention.

FIG. 5 shows a screenshot and related audio that may occur during an exemplary troubleshooting session. Box 160 shows a video of the TSR, and indicates that the drawing tool has been selected. Image 160 is an image that has been captured via the mobile device camera of the internals of an analyzer related to a vacuum error being troubleshot. Status box 172 can indicate that the user has control of the drawing tool. Shape 174 has been drawn via the touchscreen of the mobile device by the user to highlight a portion of the image for discussion. Instruction box 176 indicates the current step being undertaken, which may be driven by a predetermined script or selected by the TSR. Status information box 178 indicates sensor information relevant to the step that is being reported in substantially real-time from the analyzer to the mobile device and/or the TSC. In this example, the vacuum system is being diagnosed, so that vacuum sensor information may be particularly relevant.

FIG. 6 shows an exemplary screen shot during a tutorial or troubleshooting session with a TSR. In this example, the tutorial or TSR has selectively zoomed the image onto a vacuum gauge. Where FIG. 6 relates to a live troubleshooting session, box 160 includes video footage of the TSR. It should be appreciated, that box 160 is optional for live troubleshooting sessions in various embodiments. Image 180 is an image captured by the mobile device, showing internals of the analyzer. Box 182 indicates that the TSR has control of image manipulation at the moment. In this example, the TSR has selectively zoomed in on a vacuum dial by selecting portion 184 of image 180. Portionl84 is blown up in image 186, allowing both the TSR and the user to read a vacuum gauge. Instruction bubble 188 indicates the current step, which requires reading the gauge level. Query 188 allows the user to selectively enter the vacuum level that he reads from the gauge. In this example, the analyzer may not have a digital sensor capable of reading the vacuum level, requiring the user to manually read the gauge and input the level. It should be appreciated, that a similar interaction could occur during a tutorial equipped with AR capabilities or during a live session.

In some embodiments, the user of application 26 can selectively enable front and rear cameras, allowing the user to select whether to have face-to-face communication with the TSR and whether to share images from the rear camera. Accordingly, in some embodiments, during some troubleshooting sessions, an image of the TSR can occupy substantially all of the mobile device screen when no image is being discussed.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A system for troubleshooting IVD equipment, comprising:
   a processor configured to receive sensor data pertaining to a status of the IVD equipment and to transmit the sensor data in substantially real-time to at least one of a mobile device and a remote technical support center; and
   one or more memory devices containing software instructions to configure the mobile device to:
      facilitate a call between a user of the IVD equipment and a representative at the remote technical support center;
      display one or more images to the user at substantially the same time that the representative can see the one or more images; and
      receive at least one command from the representative to change the one or more images displayed to the user.

2. The system of claim 1, wherein the at least one command comprises one or more commands to allow the representative to emphasize a portion of the one or more images.

3. The system of claim 1, wherein the one or more images comprise at least one image captured by a camera on the mobile device.

4. The system of claim 3, wherein the at least one command comprises one or more commands to allow the representative to instruct the mobile device to do at least one of:
   performing a zoom function on the camera and turning on a light to illuminate the image plane of the camera.

5. The system of claim 1, wherein the software instructions further comprise instructions to enable user and the representative to see one another during the call.

6. The system of claim 1, further comprising a processor at the technical support center configured to record an interaction between the representative and the user.

7. The system of claim 1, wherein the software instructions further comprise instructions to present a pre-recorded tutorial to the user.

8. A method for assisting a user in troubleshooting IVD equipment, comprising steps of:
   receiving sensor data pertaining to the status of the IVD equipment in substantially real-time at least one of a mobile device and a remote technical support center;
   facilitating, via software instructions on a mobile device, a call between a user and a representative at the remote technical support center;
   displaying one or more images to the user at substantially the same time that the representative can see the one or more images; and
   receiving at least one command from the representative to change the one or more images displayed to the user.

9. The method of claim 8, wherein the at least one command comprises one or more commands to allow the representative to emphasize a portion of the one or more images.

10. The method of claim 8, wherein the one or more images comprise at least one image captured by a camera on the mobile device.

11. The method of claim 10, wherein the at least one command comprises one or more commands to allow the representative to instruct the mobile device to do at least one of:
    performing a zoom function on the camera and turning on a light to illuminate the image plane of the camera.

12. The method of claim 8, wherein the step of facilitating a call further comprises enabling user and the representative to see one another during the call.

13. The method of claim 8, further comprising recording an interaction between the representative and the user.

14. The method of claim 8, further comprising presenting a pre-recorded tutorial to the user.

15. A method for assisting a user in troubleshooting IVD equipment, comprising steps of:
    receiving sensor data pertaining to the status of the IVD equipment in substantially real-time at a mobile device;
    requesting a first tutorial from a stored plurality of tutorials, in response to user input of the mobile device, wherein the first tutorial includes a plurality of pictures or videos to be displayed on a screen of the mobile device;
    determining, based on the sensor data if a first step of the tutorial has been completed by the user;
    advancing to a second step in the tutorial in response to the determining step;
    determining, by the mobile device, if an error condition exists upon completion of a last step of the first tutorial; and
    connecting the user with a representative at a remote technical support center, wherein the representative receives the sensor data and can view one or more images on the mobile device screen.

16. The method of claim 15, further comprising receiving, at the mobile device, one or more commands to allow the representative to draw on one or more images presented on the mobile device screen.

17. The method of claim 15, wherein the one or more images comprise at least one image captured by a camera on the mobile device.

18. The method of claim 17, further comprising receiving, at the mobile device, one or more commands to allow the representative to instruct the mobile device to do at least one of:
  performing a zoom function on the camera and turning on a light to illuminate the image plane of the camera.

19. The method of claim 15, further comprising recording an interaction between the representative and the user.

20. The method of claim 15, further comprising presenting to the user a second tutorial relating to a possible root cause based on the determining step.

\* \* \* \* \*